(12) United States Patent
Axelrod et al.

(10) Patent No.: US 9,801,800 B2
(45) Date of Patent: Oct. 31, 2017

(54) COMPOSITIONS FOR IMPROVING THE ORAL HEALTH OF ANIMALS, METHODS USING SAME, AND PET TREATS INCORPORATING THE SAME

(71) Applicant: T.F.H. PUBLICATIONS, INC., Neptune City, NJ (US)

(72) Inventors: Glen S. Axelrod, Colts Neck, NJ (US); Ajay Gajria, Maharashtra (IN)

(73) Assignee: T.F.H. PUBLICATIONS, INC., Neptune City, NJ (US)

( * ) Notice: Subject to any disclaimer, the term of this patent is extended or adjusted under 35 U.S.C. 154(b) by 0 days.

(21) Appl. No.: 14/817,801

(22) Filed: Aug. 4, 2015

(65) Prior Publication Data
US 2016/0184209 A1    Jun. 30, 2016

Related U.S. Application Data

(62) Division of application No. 13/286,016, filed on Oct. 31, 2011, now Pat. No. 9,095,517.

(51) Int. Cl.
| | | |
|---|---|---|
| *A61K 8/24* | (2006.01) | |
| *A61K 8/67* | (2006.01) | |
| *A61K 8/73* | (2006.01) | |
| *A61K 8/99* | (2017.01) | |
| *A61Q 11/00* | (2006.01) | |
| *A23K 20/174* | (2016.01) | |
| *A23K 20/163* | (2016.01) | |
| *A23K 20/26* | (2016.01) | |
| *A23K 50/42* | (2016.01) | |

(52) U.S. Cl.
CPC ............ *A61K 8/676* (2013.01); *A23K 20/163* (2016.05); *A23K 20/174* (2016.05); *A23K 20/26* (2016.05); *A23K 50/42* (2016.05); *A61K 8/24* (2013.01); *A61K 8/73* (2013.01); *A61K 8/99* (2013.01); *A61Q 11/00* (2013.01)

(58) Field of Classification Search
None
See application file for complete search history.

(56) References Cited

U.S. PATENT DOCUMENTS

| | | |
|---|---|---|
| 5,296,217 A | 3/1994 | Stookey |
| 5,618,518 A | 4/1997 | Stookey |
| 6,379,725 B1 * | 4/2002 | Wang ............... A01K 15/026 426/104 |
| 6,670,343 B1 | 12/2003 | Ito et al. |
| 6,799,536 B1 | 10/2004 | Jia et al. |
| 7,777,027 B2 | 8/2010 | Bahl et al. |
| 2003/0194380 A1 | 10/2003 | Szymaitis |
| 2005/0008759 A1 | 1/2005 | Nie et al. |
| 2005/0214349 A1 * | 9/2005 | Nie ..................... A23K 40/20 424/442 |
| 2006/0243219 A1 | 11/2006 | Brown |
| 2010/0183523 A1 | 7/2010 | Wagner |
| 2010/0303978 A1 | 12/2010 | Sunvold et al. |
| 2011/0150789 A1 | 6/2011 | Andersen |

FOREIGN PATENT DOCUMENTS

| | | |
|---|---|---|
| EP | 1 127 572 | 8/2001 |
| WO | 00/13521 | 3/2000 |

OTHER PUBLICATIONS

International Search Report and Written Opinion from related PCT Appln. No. PCT/US12/59863 dated Dec. 20, 2012.
Jessica Taylor, "In Plain Sight", Petfood Industry, vol. 52, No. 3, Mar. 31, 2010, pp. 70-72, Wolcott, New York, retrieved from: http://www.petfoodindustry.com/ext/resources/uploadedfiles/PetfoodIndustry/petfoodindustry201003-d1.pdf.
Extended European Search Report from related EP Appln. No. 12845711.6 dated Aug. 5, 2015.

* cited by examiner

*Primary Examiner* — Gigi Huang
(74) *Attorney, Agent, or Firm* — Grossman, Tucker, Perreault & Pfleger, PLLC

(57) ABSTRACT

Described herein are dental compositions, articles of manufacture including such dental compositions, and methods of using such dental compositions. In some embodiments, the dental compositions include a combination of ascorbic acid with at least one of a hexametaphosphate and a beta glucans. In some instances, the dental compositions are included within an edible article, a chew, or an edible chew. Administration of the dental compositions to the oral cavity of a subject may reduce the gingival, plaque, and/or calculus scores of the subject over a defined time period.

8 Claims, 10 Drawing Sheets

COMPOSITIONS FOR IMPROVING THE ORAL HEALTH OF ANIMALS, METHODS USING SAME, AND PET TREATS INCORPORATING THE SAME

CROSS-REFERENCE TO RELATED APPLICATIONS

This application is a divisional application of U.S. application Ser. No. 13/286,016 filed on Oct. 31, 2011 which is fully incorporated herein by reference.

FIELD OF THE INVENTION

The present disclosure relates generally to compositions for improving the oral health of animals, methods using the same, and pet treats incorporating the same.

BACKGROUND

Dental calculus, or tartar, is recognized as a recurring calcified deposit on the surfaces of the teeth of animals, including humans and domestic animals such as dogs and cats. Generally, dental calculus develops in a sequential process that involves calcification of accumulated dental plaque by saliva. Although dental calculus may not be directly responsible for the development of oral disease, it is recognized as contributing to the development of periodontal disease. Among other things, dental calculus can irritate adjacent soft tissues of the mouth, thereby instigating an inflammatory response. Moreover, dental calculus can interfere with normal tooth cleaning processes that occur during mastication, and may harbor bacterial toxins that exacerbate the development of periodontal disease.

More specifically, dental calculus is recognized as contributing the development of gingivitis, a non-destructive form of periodontal disease. Left untreated, gingivitis may progress to periodontitis, a destructive form of periodontal disease. The prevention/treatment of dental calculus and gingivitis is therefore important, because of the contribution of such conditions to the development of more significant oral health problems.

There are various recognized approaches for preventing the formation of calculus, including the meticulous periodic removal of dental plaque prior to calculus formation, and periodic application of crystal growth inhibiting compounds that hinder the calcification of dental plaque by saliva. While these methods are effective to some degree, additional and potentially more effective methodologies for addressing dental calculus and subsequent oral health problems (e.g., gingivitis) are needed, particularly with respect to products aimed at improving the oral health of animals such as dogs and cats.

The present disclosure addresses one or more of these needs by providing dental compositions containing a novel combination of a hexametaphosphate with at least one of ascorbic acid and at least one beta glucans. Also described herein are methods of using such dental compositions, and articles of manufacture including such dental compositions.

SUMMARY

One aspect of the present disclosure relates to dental compositions. In some embodiments, the dental compositions include ascorbic acid in combination with at least one of a hexametaphosphate (HMP) and a beta glucans. The ascorbic acid may be present in the dental compositions in a amount ranging from greater than 0 to about 5 weight %, the HMP may be present in an amount ranging from greater than 0 to about 5 weight %, and the at least one beta glucans may be present in an amount ranging from greater than 0 to about 1.0 weight %. In some embodiments, the dental compositions described herein include a combination of ascorbic acid, HMP, and beta glucans.

Also described herein are pet chews including a base composition and a dental composition. The dental composition may be incorporated into the base composition. In some embodiments, the base composition includes a starch, and the dental composition includes a combination of ascorbic acid, hexametaphosphate, and beta glucans.

Methods of using the dental compositions of the present disclosure are also provided herein. In some embodiments, the methods include administering a dental composition to an animal, wherein the dental composition includes at least one of ascorbic acid, a hexametaphosphate, at least one beta glucans, and combinations thereof. In some embodiments, the methods include administering a dental composition that includes a combination of ascorbic acid, HMP and at least one beta glucans to an animal, wherein the concentration ascorbic acid, HMP, and/or beta glucans is effective to treat at least one of gingivitis and dental calculus in an animal.

DETAILED DESCRIPTION

Figure 1:
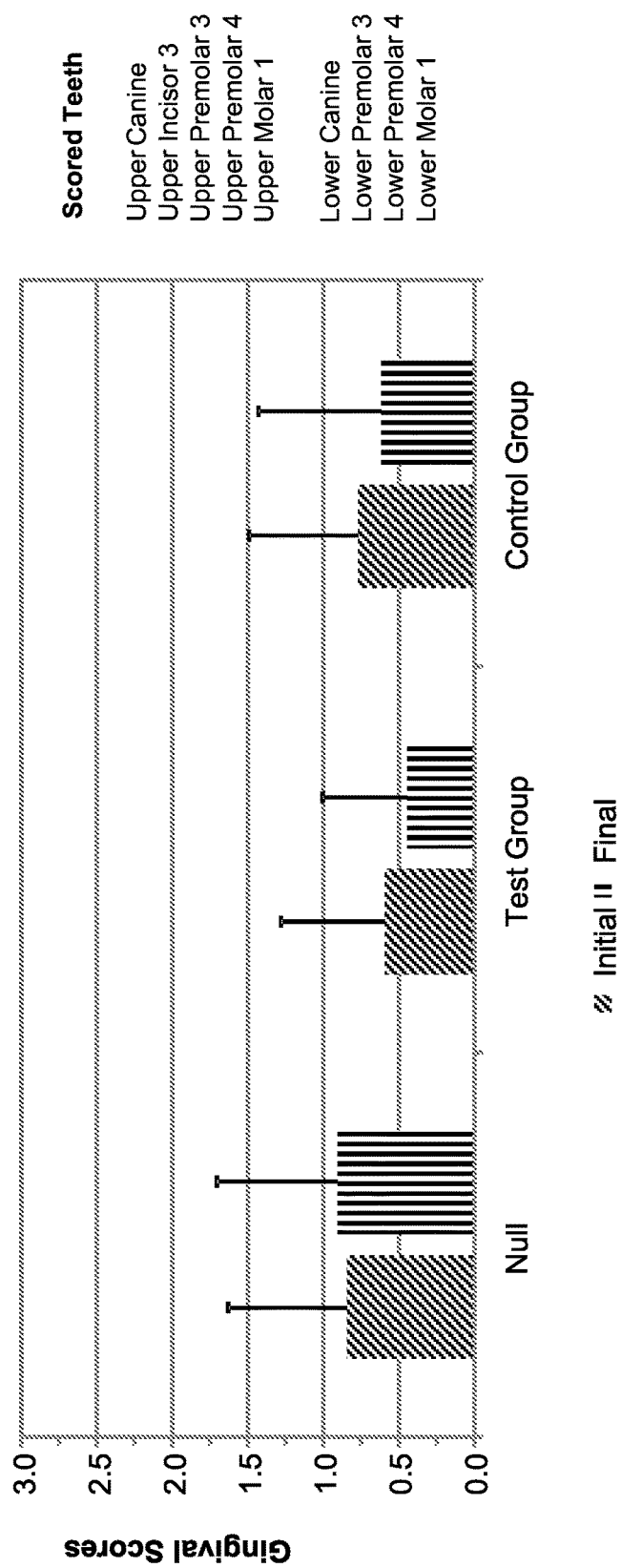
FIG. 1 is a bar graph plotting the gingival scores of dogs that were administered no bone (null), a control bone (control group) group, and a test bone (test group) containing a dental composition in accordance with one embodiment of the present disclosure.

As used herein, the term "about" when used in the context of an amount means+/−5% of the stated amount.

As used herein, the term "beta glucans" means any of a variety of polysaccharides that contain glucose monomer units bonded by beta linkages.

As used herein, the term "calculus" means dental plaque that has partially or completely calcified.

As used herein, the terms "chew" and "chew product" are interchangeably used to mean a product that intended for chewing by an animal for an extended period of time, e.g., for several minutes, several hours, or even one or more days.

As used herein, the term "edible article" means a product that is fit to be ingested by an animal.

As used herein, the term "effective amount" when used in the context of an agent or agents (e.g., a dental composition or its respective components), means the amount of agent or agents is sufficient to treat at least one of calculus, plaque, and gingivitis in a subject. As will be understood in the art, the effective amount of an agent (e.g., a dental composition or its components) may vary based on the component, the nature and severity of the condition to be treated, the age and condition of the subject to be treated, and other factors.

As used herein, the terms "reducing," "reduce," "reduces," and "reduction" in reference to calculus, plaque, gingivitis, and combinations thereof means that: a lower amount of at least one of calculus, plaque, and gingivitis is found on or about at least one tooth of an subject after administration of the dental compositions in accordance with the present disclosure; or that at least one of calculus, plaque, and gingivitis is completely removed or ameliorated on or about at least one tooth of a subject after administration of the dental compositions in accordance with the present disclosure.

The term, "prevent" when used in reference to calculus, plaque, and gingivitis, means that less calculus, plaque, and gingivitis is observed over a period of time in subjects to which a dental composition in accordance with the present disclosure is administered, relative to similar subjects that have not received a dental composition in accordance with the present disclosure over the same period of time.

The terms "treat" and "treating" in the context of to calculus, plaque, and gingivitis are used interchangeably herein to mean preventing, reducing, and/or removing at least one of plaque, dental calculus, and gingivitis in a subject (e.g., a cat, a dog, a human, etc.).

In many instances, the present disclosure uses ranges to describe features such as the amount, concentration, and dosage rate of various components. It should be understood that such ranges are exemplary, and that in reciting a range the present disclosure contemplates and encompasses all iterative values between the respective endpoints of that range. Accordingly, while the present dislcosure may recite only the endpoints of a range, that range should be interpreted as expressly reciting all iterative values between the stated endpoints.

One aspect of the present disclosure relates to dental compositions that include a combination of a hexametaphosphate (HMP) with at least one of ascorbic acid, at least one beta glucans, and combinations thereof. Also described herein are articles of manufacture incorporating such dental compositions, and methods for using such dental compositions.

Any type of HMP may be used in the dental compositions of the present disclosure. As examples of types of HMP that can be used, non-limiting mention is made of the hexametaphosphates of calcium, potassium, sodium, and combinations thereof. In some embodiments, the dental compositions of the present disclosure contain sodium hexametaphosphate.

The amount of HMP included in the dental compositions described herein may vary widely. For example, HMP may be present in the dental composition in an amount ranging from greater than 0 to about 10 weight %, such as from greater than 0 to about 5 weight %, about 0.5 to about 4.5 weight %, about 1 to about 4 weight %, or even from about 2 to about 4 weight %. In some embodiments, the dental compositions of the present disclosure contain about 3.0-3.25 weight % HMP (e.g., NAHMP), such as about 3.1 weight % HMP.

In addition to HMP, the dental compositions of the present disclosure can contain ascorbic acid. For example, ascorbic acid can be present in the dental compositions of the present disclosure in an amount ranging from greater than 0 to about 10 weight %, such as greater than 0 to about 5 weight %, greater than 0 to about 1 weight %, or even about 0.1 to about 0.5 weight %. In some embodiments, the dental compositions of the present disclosure contain ascorbic acid in an amount ranging from 0.15 to about 0.25 weight %, such as 0.20 weight %.

The dental compositions of the present disclosure may also contain at least one beta glucans. For example, at least one beta glucans may be present in the dental compositions of the present disclosure in an amount ranging from greater than 0 to about 5 weight %, such as greater than 0 to about 1 weight %, greater than 0 to about 0.5 weight % or even about 0.1 to about 0.25 weight %. In some embodiments, the dental compositions described herein contain about 0.1 weight % of at least one beta glucans.

The at least one beta glucans may be derived from any source, including natural and genetically modified sources. For example, the at least one beta glucans may be extracted from a natural or genetically modified source. As non-limiting examples of such natural or genetically modified sources, mention is made of yeasts, mushrooms, and grains. In some embodiments, the dental compositions described herein contain at least one beta glucans derived from yeast, such as *saccharomyces cerevisiae* (also known as brewers yeast). And in some cases, the at least one beta glucans is composed solely of beta glucans derived (e.g., extracted) from *saccharomyces cerevisiae*.

While *saccharomyces cerevisiae* is a convenient source of beta glucans, beta glucans derived from other yeast and non-yeast sources may also be used in the dental compositions of the present disclosure. For example, the dental compositions described herein may include beta glucans derived from at least one of *saccharomyces delbrueckii, saccharomyces rosei, saccharomyces microellipsodes, saccharomyces carlbergensis, saccharomyces bisporus, saccharomyces fermentati, saccharomyces rouxii, schizosaccharomyces pombe, schizophylium commune, scierotium glucanium, lentinus edodes, kluyveromyces lactis, kluyveromyces fragilis, kluyveromyces polysporus, candida albicans, candida cloacae, candida tropicalis, candida utilis, hansenula wingei, hansenula arni, hansenula henricii, hansenula americana, hansenula canadiensis, hansenula capsulata, hansenula polymorpha, pichia rhodanensis, pichia ohmeri, torulopsis bovina, torulopsis glabrata*, and combinations thereof.

The amount of HMP, ascorbic acid, and/or beta glucans included in the dental compositions of the present disclosure may be adjusted so as to provide a desired dose when the dental composition is administered to a subject. With respect to HMP, for example, the dental compositions can be formulated so as to provide an HMP dose of greater than 0 to about 125 mg/kg body weight, such as from about 1 to about 100 mg/kg body weight, about 25 to about 100 mg/kg body weight, about 50 to about 90 mg/kg body weight, or even about 75 to about 90 mg/kg body weight. In one non-limiting embodiment, a dental composition is formulated to provide an HMP dose of about 84 mg/kg body weight.

In the case of ascorbic acid, the dental compositions described herein can be formulated so as to provide an ascorbic acid dose of greater than 0 to about 10 mg/kg body weight, such as greater than 0 to about 7.5 mg/kg body weight, about 1 to about 5 mg body weight, or even about 2 to about 4 mg/kg body weight. In one non-limiting embodiment, a dental composition is formulated so as to provide an ascorbic acid dose of about 4 mg/kg body weight.

With respect to beta glucans, the dental compositions described herein can be formulated so as to administer at least one beta glucans to a subject at a dose of greater than 0 to about 10 mg/kg body weight, such as greater than 0 to about 5 mg/kg body weight, about 0.5 to about 4 mg/kg body weight, or even about 1 to about 3 mg/kg body weight. In some embodiments, the dental compositions are formulated to administer at least one beta glucans to a subject at a dose of about 2 mg/kg body weight.

As will be described in detail below, the dental compositions of the present disclosure may be incorporated into an article of manufacture, such as but not limited to a chew product and/or an edible article. In such instances, the amount of beta glucans in the article of manufacture can be sufficient to provide a dose consistent with the foregoing ranges via the mastication and/or oral ingestion of the article by a subject (e.g., a human or non-human animal).

In non-limiting embodiments, the dental compositions described herein include a combination of HMP and ascorbic acid, such as a combination of sodium hexametaphosphate and ascorbic acid. In such embodiments, the relative amounts of HMP and ascorbic acid may fall within the previously recited ranges.

Accordingly, the present disclosure contemplates dental compositions containing HMP in an amount ranging from greater than 0 to about 10 weight % (such as from greater than 0 to about 5 weight %, about 0.5 to about 4.5 weight %, about 1 to about 4 weight %, or even from about 2 to about 4 weight %), and ascorbic acid in an amount ranging from greater than 0 to about 10 weight % (such as greater than 0 to about 5 weight %, greater than 0 to about 1 weight %, or even about 0.1 to about 0.5 weight %). In some embodiments, the dental compositions contain about 3.0 to about 3.25 weight % HMP and about 0.15 to about 0.25 weight % ascorbic acid.

In further non-limiting embodiments, the dental compositions described herein include a combination of HMP and at least one beta glucans, such as a combination of sodium hexametaphosphate and beta glucans derived from a yeast source (e.g., *saccharomyces cerevisiae*). In such embodiments, the relative amounts of HMP and beta glucans may fall within the previously recited ranges.

Thus, for example, the present disclosure contemplates dental compositions containing HMP in an amount ranging from 0 to about 10 weight % (such as from greater than 0 to about 5 weight %, about 0.5 to about 4.5 weight %, about 1 to about 4 weight %, or even from about 2 to about 4 weight %), and at least one beta glucans in an amount ranging from greater than 0 to about 5 weight % (such as greater than 0 to about 1 weight %, greater than 0 to about 0.5 weight % or even about 0.1 to about 0.25 weight %). In some embodiments, the dental compositions contain about 3.0 to about 3.25 weight % HMP and about 0.1 to about 0.25 weight % beta glucans.

In additional non-limiting embodiments, the dental compositions of the present disclosure contain a combination of HMP (e.g., sodium hexametaphosphate), ascorbic acid, and at least one beta glucans (e.g., from a yeast such as *saccharomyces cerevisiae*). In such embodiments, the relative amounts of HMP, ascorbic acid, and beta glucans may fall within the previously recited ranges.

Thus, for example, the present disclosure contemplates dental compositions containing HMP in an amount ranging from 0 to about 10 weight % (such as from greater than 0 to about 5 weight %, about 0.5 to about 4.5 weight %, about 1 to about 4 weight %, or even from about 2 to about 4 weight %), ascorbic acid in an amount ranging from greater than 0 to about 10 weight % (such as greater than 0 to about 5 weight %, greater than 0 to about 1 weight %, or even about 0.1 to about 0.5 weight %), and at least one beta glucans in an amount ranging from greater than 0 to about 5 weight % (such as greater than 0 to about 1 weight %, greater than 0 to about 0.5 weight % or even about 0.1 to about 0.25 weight %). In some non-limiting embodiments, the dental composition contains about 3.0 to about 3.25 weight % HMP, about 0.15 to about 0.25 weight % ascorbic acid, and about 0.1 to about 0.25 weight % of at least one beta glucans. And in a specific non-limiting embodiment, the dental compositions described herein contain about 3.1 weight % sodium hexametaphosphate, about 0.2 weight % ascorbic acid, and about 0.1 weight % beta glucans (e.g., derived from *saccharomyces cerevisiae*).

The dental compositions of the present disclosure may also contain a breath freshening agent. As an example of a suitable breath freshening agent, non-limiting mention is made of chlorophyll, mint, and essential oils. When used, the breath freshening agent may be included in the dental composition in an amount ranging from greater than 0 to about 5 weight %, such as about 0.1 to about 2.5 weight %, about 0.1 to about 1 weight %, or even about 0.1 to about 0.5 weight %.

The dental compositions of the present disclosure may also include a mushroom matrix formed from one or more species of mushroom. In some embodiments, the mushroom matrix is composed of equal parts of multiple mushroom species. For example, the mushroom matrix may be composed of equal parts (e.g., 20 weight %) of five mushroom species, namely king trumpet (*pleurotus eryngii*), reishi (*ganoderma lucidum*) cordyceps (*cordycepts militaris*),

*antrodia*(*antrodia camphorata*), and *shiitake* (*lentinula edodes*). When used, the mushroom matrix may be present in the dental composition in an amount ranging from greater than 0 to about 10 weight %, such as about 1 to about 5 weight % of the dental composition.

The dental compositions of the present disclosure can be administered to a wide variety of animals. As non-limiting examples of such animals, mention is made of bears, cats, dogs, elephants, equines (e.g., horses, zebras, etc.), ferrets, humans, leopards, lions, and primates (e.g., apes, chimpanzees, gorillas, orangutans, etc.). However, it should be understood that the dental compositions described herein may be administered to any type of animal. In some non-limiting embodiments, the dental compositions of the present disclosure are administered to a dog, a cat, or a human.

Another aspect of the present disclosure relates to articles of manufacture that include the dental compositions described herein. As non-limiting examples of such articles, mention is made of chew products and edible articles, as defined above. It should be understood that regardless of their form, the articles of manufacture described herein can function to remove, prevent, and/or treat at least one of dental plaque, calculus, and gingivitis when masticated and/or ingested by a subject.

With respect to chew products, the present disclosure envisions any of a variety of products that are intended for chewing by an animal for an extended period of time. Thus, for example, the chew products may take the form of a bar, a bone, a chewing gum, a strip, a nugget (pellet), a geometric or non-geometric shape (e.g., a "bone" or a portion thereof, a roll, a ball, a cube, a ring, a rope, etc.), or a toy. In some embodiments, the chew products are intended for animal chewing, such as a by a dog, a cat, or another non-human domestic or wild animal.

With regard to edible articles, the present disclosure envisions any of a variety of products that are suitable for consumption by a human or non-human animal. As non-limiting examples of such edible articles, mention is made of edible bars, strips, kibble, biscuits, and dry pet food. In some instances, the edible articles are designed for consumption by a non-human animal, such as a dog, a cat, or other non-human domestic or wild animal. Accordingly, it should be understood that in some embodiments, the articles of the present disclosure can serve as a food for a subject. And in some instances, the articles of the present disclosure can function primarily as a food for a subject.

It should be understood that while the present disclosure makes distinct reference to edible articles and chews, it is possible for an article of manufacture to qualify as both an edible article and a chew. This is particularly true in the case of products designed for animals such as dogs, where the animal may ingest all or a portion of an article that is otherwise designed for chewing. Thus, in some embodiments of the present disclosure, the dental compositions may be incorporated into an edible chew product.

In some embodiments, the articles of manufacture include a base composition into which a dental composition according to the present disclosure can be added. In some embodiments, the base composition includes one or more "primary ingredients." As used herein, the term "primary ingredient" means an ingredient other than water that is present in an amount greater than about 30 weight % of the base composition. For example, the base composition may include a primary ingredient in an amount greater than about 50 weight %, such as greater than about 75 weight %, greater than about 90 weight %, greater than about 95 weight %, or even greater than about 98 weight % of the base composition.

A wide variety of materials may be used as primary ingredients in the base compositions of the present disclosure. As examples of such primary ingredients, non-limiting mention is made of starches, polymers (e.g., nylon, kevlar, rubber), animal skin (e.g., rawhide), and wood.

In some embodiments, the base composition includes at least one starch. The at least one starch may be any carbohohydrate of natural or vegetable origin. The starch may include amylose and/or amylopectin, and may be extracted from plants including, but not limited to potatoes, rice, tapioca, corn, and cereals such as rye, wheat, and oats. The starch may also be extracted from fruits, nuts and rhizomes, arrowroot, guar gum, locust bean, arracacha, buckwheat, banana, barley, cassava, konjac, kudzu, oca, sago, sorghum, sweet potato, taro, yams, fava beans, lentils and peas. The starch may be initially provided in particulate or powder form, which may be understood as milled and/or pre-sifted.

In some embodiments of the present disclosure, the edible base composition includes wheat starch as a primary ingredient. As a non-limiting example of a suitable wheat starch that may be used, mention is made of the wheat starch products sold by Manildra Group USA under the tradenames GEMSTAR 100 (a food grade wheat starch, GEMSTAR 100+(a food grade wheat starch), GEM OF THE WEST VITAL WHEAT GLUTEN (a powder product produced by low temperature drying of gluten extracted from organic wheat flour); ORGANIC GEMSTAR 100 (a wheat starch extracted from organic wheat flour); and ORGANIC GEM-GEL 100 (a pregelatinized wheat starch). Additional non-limiting mention is made of the resins sold by ADM under the trade names EDIGEL 100 (a wheat resin composition) and AYTEX P (an unmodified food grade wheat starch).

The base composition may also include cellulose. The cellulose may be, for example, a long-chain polymer of polysaccharide carbohydrate. The cellulose may also be derived or extracted from plants. The cellulose may be incorporated into the base composition between about 1-15% by weight of the base composition and any increment or value therebetween including 4%, 10%, 11%, etc.

Emulsifiers or surfactants may also be included in the base composition. The emulsifier may be present between about 1-10% by weight of the base composition. As non-limiting examples of suitable emulsifiers, mention is made of lecithin, which may be extracted or derived from, for example, egg yolk or soy beans.

The base composition may also include a plasticizer, such as but not limited to glycerin. The plasticizer may be included in the base composition in an amount ranging from greater than 0 to less than 30 weight % of the base composition, such as between about 10 to 30 weight % or even between about 15 to 30 weight % of the base composition.

The base composition may also include a humectant, such as but not limited to oat fiber. The humectant may be included in the base composition in an amount ranging from about 0.1 to about 5% by weight of the base composition. As used herein, the term "humectant" means an additive that can absorb water in the base composition.

The base composition may also include water. The amount of water in the base composition may vary before and after formation of an article of manufacture. For example, prior to the formation of an article of manufacture, water may be present in an amount ranging from greater than 0 to about 40 weight % of the base composition. After the article of manufacture has been formed, water may be present in the base composition in an amount ranging from greater than 0 to about 20 weight %, such as about 1 to about 20%, about 1 to about 10 weight %, or even about 1 to about 5 weight %.

The base composition may include a nutraceutical, such as but not limited to a fermented soya nutraceutical. As non-limiting examples of suitable nutraceuticals, mention is made of the fermented soya nutraceuticals sold by Bio Food, Ltd., Pine Brook, N.J. under the general trademark SOYNATTO®. The nutraceutical may be present in an amount ranging from about 0.01 to less than 30% by weight of the base composition, such as about 0.1 to less than 30 weight %, about 0.1 to about 10 weight %, or even about 0.1 to about 1 weight % of the base composition.

The base composition may also contain one or more additives. As non-limiting examples of such additives, mention is made of flours, fruit matter, gums (e.g., guar gum), nuts, nut bits or nut flour such as peanut flour, minerals, palatability enhancers, vegetable matter, vitamins (other than vitamin C) and animal or fish products, animal or fish by-products, animal or fish meal, animal or fish digests, and combinations thereof. Gluten may also be incorporated into the base composition. Gluten may be understood as water-insoluble protein complex extracted from cereal grains such as maize or corn and wheat. These additives may be present individually in amounts less than 30 weight %, but cumulatively in amounts ranging from greater than 0 to about 50% by weight of the base composition.

One or more flavorants, herbs, herbal extracts, minerals, colorants, yeast products (other than beta glucans), soy products (other than SOYNATTO®), and attractants may also be incorporated into the base composition. Attractants generally include compounds that may increase an animal's interest in the base composition, and may include compounds previously identified herein as additives, such as an animal or fish digest. Such flavorants, herbs, herbal extracts, additives may be present individually or cumulatively in amounts ranging about greater than 0 to about 25% by weight of the base composition, and any increment or value there between. For example, they may be included in amounts ranging from about 0.01-25%, about 0.1-0.5, about 1 to about 10%, and even about 10 to about 20% by weight. The base composition may also include calcium carbonate in an amount ranging from greater than 0 and about 10 weight %, such as about 1 to about 5 weight %.

As noted above, the dental compositions of the present disclosure may be incorporated into a base composition, such as those described above. By "incorporated into," it is meant that the dental composition is present within or is surrounded by the base composition. Accordingly, the present disclosure contemplates articles of manufacture which include a dental composition and a base composition in the form of a mixture, a solution, a colloid, a dispersion, an emulsion, etc. It should therefore be understood that in some embodiments of the present disclosure, the dental compositions are not present in an article of manufacture as a coating on a base composition.

The amount of dental composition added to the base composition may vary widely. In some embodiments, a sufficient amount of dental composition is added to the base composition such that HMP, ascorbic acid, beta glucans, chlorophyll, mushroom matrix, and combinations thereof are present in amounts correlating to the previously recited weight percentages for such components, relative to the total weight of the article of manufacture. Thus, for example, the present disclosure contemplates articles of manufacture wherein HMP is present in an amount ranging from greater than 0 to about 10 weight %, such as from greater than 0 to about 5 weight %, about 0.5 to about 4.5 weight %, about 1 to about 4 weight %, or even from about 2 to about 4 weight %, relative to the total weight of the article of manufacture.

The articles of manufacture may be made using any known process for manufacturing a chew product or an edible article. For example, the articles of manufacture may be produced using injection molding, extrusion, and combinations thereof. In some embodiments, the articles of manufacture are formed by extrusion followed by injection molding. In other non-limiting embodiments, the articles of manufacture are formed by direct injection molding. In either case, the dental composition may be incorporated into the base composition prior to or after the introduction of the ingredients of the base composition into an extruder or injection molding machine.

Another aspect of the present disclosure relates to methods of treating at least one oral condition with the dental compositions and articles of manufacture described herein. In some embodiments, the methods include administering an effective amount of a dental composition consistent with the present disclosure (or the components thereof) to a subject in need thereof, so as to treat at least one of gingivitis, plaque, calculus, and combinations thereof present in the oral cavity of said subject.

Consistent with the foregoing disclosure, the methods may administer the dental compositions described herein to the oral cavity of a subject in a variety of ways. For example, where the dental compositions are incorporated a dentifrice or similar product, it may be topically applied to the oral cavity of a subject. Such topical application may be localized to a particular region (e.g., a tooth or gingival quadrant), or may be generally applied to the entire oral cavity of the subject.

Similar to topical administration, the methods of treatment may include administering the dental compositions described herein to a patient in the form of an article of manufacture, such as an edible article, a chew, or an edible chew. In such cases, the article may be formulated so as to contain a dental composition in an effective amount to treat at least one of gingivitis, plaque, and calculus via ingestion of the article, and/or via the masticating action that occurs as the subject chews and/or ingests the article.

In some embodiments of the present disclosure, the dental compositions, articles, and methods of treatment described herein are effective to reduce, remove, or prevent a certain amount of at least one of gingivitis, calculus, plaque, and combinations thereof from the oral cavity of a subject over a defined period of time. For example, the dental compositions, articles, and methods described herein can be effective to reduce, remove, or prevent from greater than 0 to 60%, such as greater than 0 to 55%, about 10 to about 55%, about 20 to about 50%, or even about 30 to about 50% of gingivitis from the oral cavity of a subject over a defined time period. Likewise, the dental compositions, articles, and methods can be effective to reduce, remove, or prevent from greater than 0 to 60%, such as greater than 0 to 55%, about 10 to about 55%, about 20 to about 50%, or even about 30 to about 50% of plaque from a subject over a defined time period. Moreover, the dental compositions, articles, and methods may be effective to reduce, remove, or prevent from greater than 0 to 60%, such as greater than 0 to 55%, about 10 to about 55%, about 20 to about 50%, or even about 30 to about 50% of calculus from a subject over a defined time period.

The defined time period may range from one to several days, one day to several weeks, one day to one month (e.g., 28-31 days), one day to several months (e.g., 2-6 months), one day to six months, or more. In some embodiments, the defined time period is about 30 days.

The following examples serve to more fully describe dental compositions and methods of using dental compositions in accordance with the present disclosure. It should be understood that the examples are presented for illustrative purposes only, and should not be considered as limiting the scope of the invention as defined by the appended claims.

EXAMPLE 1

Animal Study Using Injection Molded Chews

To investigate the efficacy of dental compositions according to the present disclosure on the oral health of canines, a thirty day study was conducted on a pool of thirty adult greyhound dogs. During the study, the animals were housed in appropriate sized kennels with free access to water. In addition, all of the animals were fed standard greyhound feed (a kibble) on a daily basis.

Prior to the study, each animal was subjected to a physical examination, which included a hematological and serum chemistry assessment. Each animal weighed about 25-35 kg at the time they were selected, and the body weight of each animal was recorded daily over the course of the study. Gluten intolerant dogs were excluded.

To establish baseline scores for calculus, plaque, and gingivitis formation, the teeth of each animal were scaled and polished prior to the performance of the study. On the first day of the study, dental examinations were performed on each animal, and each animal was assigned dental scores based on the amount of plaque, calculus, and gingivitis observed. The pool of thirty animals was divided into three groups of ten animals, based on their baseline gingival and plaque scoring, body weight, and age.

Dogs within the first group of ten animals (hereafter, the null group) were administered normal feed over the course of the study, but did not receive any injection molded (IM) edible chews. Dogs within the second group of ten animals (hereafter the "control group") were administered normal feed, as well as IM edible chews that did not contain a dental composition (hereafter, "IM control chews"). Finally, dogs within the third group of ten animals (hereafter the test group) were administered normal feed, as well as three IM edible chews that contained a dental composition (hereafter, "IM test chews"). In the case of the control and test groups, three IM edible chews were administered each day, approximately 30 minutes before the normal feeding time for each group.

The compositions of the IM control chews and IM test chews are provided in Table 1 below. The IM test chews were formulated to provide a vitamin C dose of 4 mg/kg body weight, a beta-glucan dose of 2.0 mg/kg body weight, and an HMP dose of 84 mg/kg body weight, assuming an average body weight of 30 kg.

TABLE 1

Composition of the IM Control Chews and IM Test Chews

| Ingredient | IM Control Chew (weight %/lbs) | IM Test Chew (weight/lbs) |
| --- | --- | --- |
| Wheat Starch Beads | 96.857/1450.290 | 93.456/140.189 |
| Oat Fiber | 0.440/0.660 | 0.440/0.660 |
| Parsley Powder | 0.110/0.165 | 0.110/0.165 |
| Bacon flavor | 0.220/0.330 | 0.220/0.330 |
| Chlorophyll Liquid | 0.220/0.330 | 0.220/0.330 |

TABLE 1-continued

Composition of the IM Control Chews and IM Test Chews

| Ingredient | IM Control Chew (weight %/lbs) | IM Test Chew (weight/lbs) |
| --- | --- | --- |
| Soynatto ® | 0.140/0.210 | 0.140/0.210 |
| Nylbone ® Vitamin | 0.060/0.090 | 0.060/0.090 |
| Choline Chloride | 0.110/0.165 | 0.110/0.165 |
| Ascorbic Acid | 0.00/0.00 | 0.200/0.300 |
| Sodium Hexametaphosphate | 0.00/0.00 | 3.100/4.650 |
| Beta Glucans* | 0.00/0.00 | 0.101/0.151 |
| Water | 1.840/2.760 | 1.840/2.760 |
| Total | 100.000/300.000 | 100.000/300.000 |

*Extracted from *S. Cerevisiae*.

In general, the edible chews were well tolerated by the control group and the test group, and were consumed within the allotted period (approximately 30 minutes prior to feeding). Body weight and blood chemistry measurements taken over the course of the study showed no remarkable changes. The animals in all three groups showed no indicators of stress, and the test and control groups showed no indicators of intolerance.

On the final day of the study, each animal was subject to a dental examination, during which final scores were assigned based on the amount of plaque, calculus, and gingivitis observed. The teeth scored were the upper canine, upper incisor 3, upper premolar 3, upper premolar 4, upper molar 1, lower canine, lower premolar 3, lower premolar 4, and lower molar 1. The average initial and final scores for each group are provided in Table 2 below.

TABLE 2

Average Initial and Final Dental Scoring - IM chews

| | Null Group | | Control Group | | Test Group | |
| --- | --- | --- | --- | --- | --- | --- |
| | Initial | Final | Initial | Final | Initial | Final |
| Gingival* | | | | | | |
| Mean | 0.84 | 0.90 | 0.76 | 0.61 | 0.69 | 0.44 |
| Standard Deviation | 0.80 | 0.80 | 0.73 | 0.81 | 0.70 | 0.57 |
| Calculus* | | | | | | |
| Mean | 0.00 | 1.48 | 0.00 | 0.65 | 0.00 | 0.78 |
| Standard Deviation | 0.00 | 0.85 | 0.00 | 0.69 | 0.00 | 0.64 |
| Plaque* | | | | | | |
| Mean | 0.00 | 1.40 | 0.00 | 0.94 | 0.00 | 0.77 |
| Standard Deviation | 0.00 | 0.85 | 0.00 | 0.69 | 0.00 | 0.59 |

Figure 2:
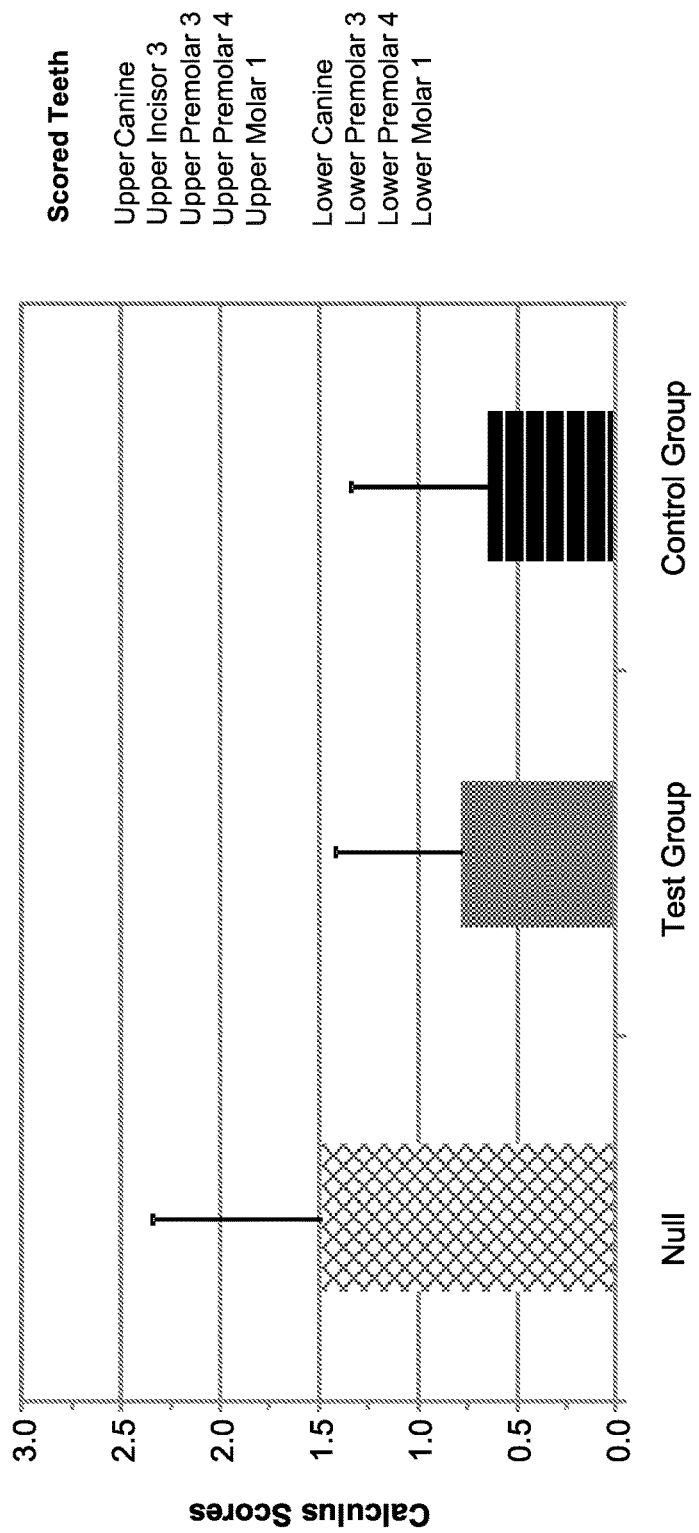
FIG. 2 is a bar graph plotting the final calculus scores of dogs that were administered no bone (null), a control bone (control group), and a test bone (test group) containing a dental composition in accordance with one embodiment of the present disclosure.
Figure 3:
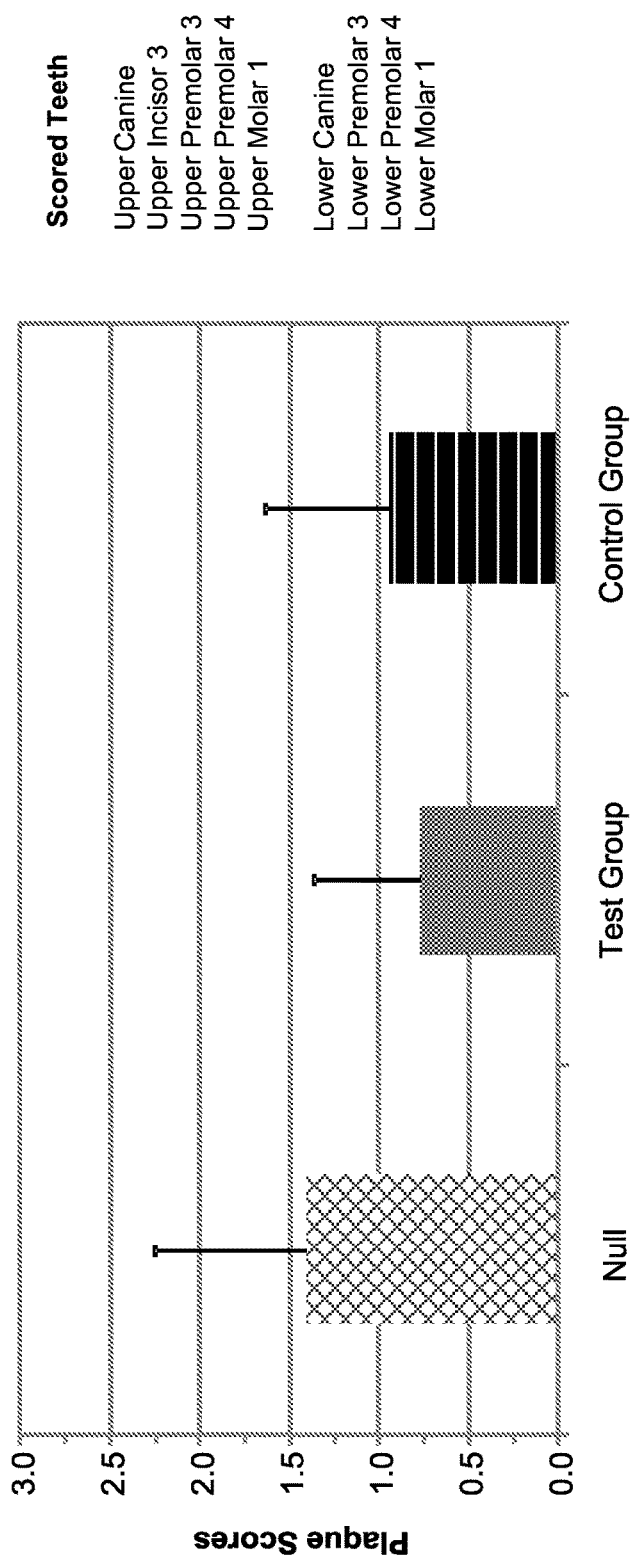
FIG. 3 is a bar graph plotting the final plaque scores of dogs that were administered no bone (null), a control bone (control group), and a test bone (test group) containing a dental composition in accordance with one embodiment of the present disclosure.

*By convention, plaque, calculus, and gingivitis range from 0 to 3
These results are presented graphically in FIGS. 1-3.

Statistical analysis was performed on the data obtained during the study. The average final gingival scores from the test group (0.44+/−0.57) were determined to be statistically different from the control group (0.61+/−0.81). In addition, average final gingival scores from the control group (0.61+/−0.81) were determined to be statistically different from the null group (0.90+/I 0.80).

Figure 4:
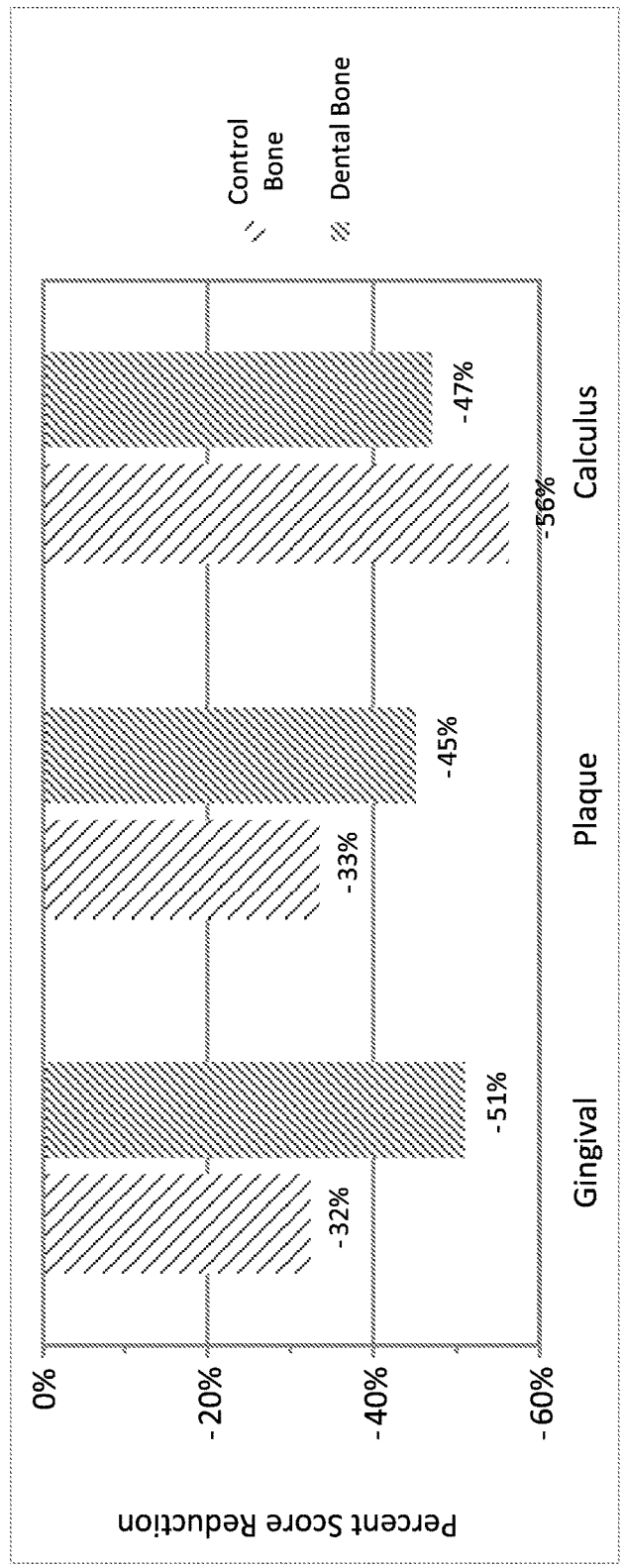
FIG. 4 is a bar graph plotting the gingival, plaque, and calculus score reductions of dogs that were administered a control bone (control group), and a test bone (test group) containing a dental composition in accordance with one embodiment of the present disclosure, relative to the corresponding scores of dogs that were administered no bone (null).
Figure 5:
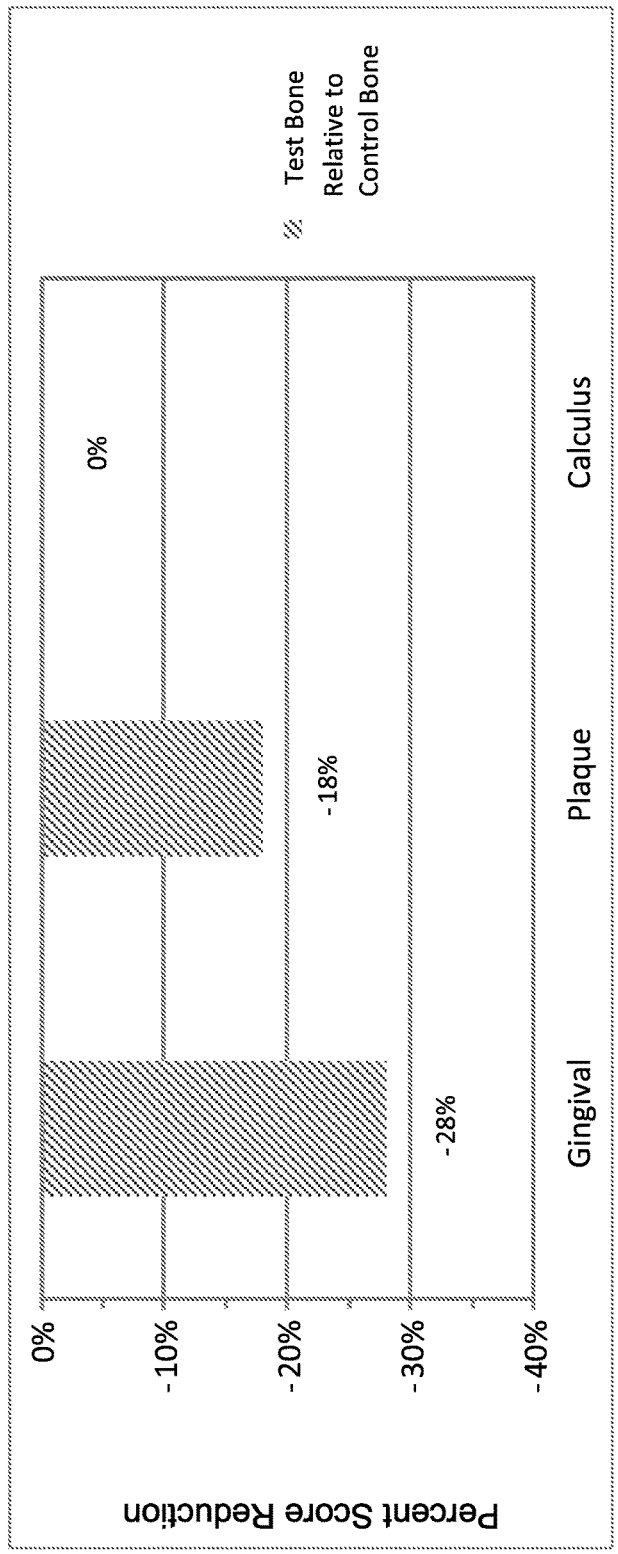
FIG. 5 is a bar graph plotting the difference between the gingival, plaque, and calculus scores of dogs administered a test bone (test group) containing a dental composition in accordance with another embodiment of the present disclosure, and corresponding scores of dogs that were administered a control bone (control group).

The performance of the IM control chews was determined by comparing the average final dental scoring (gingivitis, calculus, and plaque) of the control group to the average final dental scores of the null group. Likewise, the performance of the IM test chews was determined by comparing the average final dental scores of the test group to the average final dental scores of the null group. The results are plotted in FIGS. 4 and 5.

As shown, relative to the null group, dogs in the test group exhibited a 51% reduction in gingival score, whereas dogs in the control group exhibited a 32% reduction in gingival score. In the case of plaque, dogs in the test group exhibited a 45% reduction in plaque score relative to the null group, whereas dogs in the control group exhibited a 33% reduction in plaque score. Finally, dogs in the test group exhibited a 47% reduction in calculus score relative to the null group, whereas dogs in the control group exhibited a 56% reduction in calculus score. This data demonstrated that the IM test chews prevented or removed 28% more gingivitis and 18% more plaque relative to the IM control chews, while exhibiting comparable ability to prevent or remove calculus.

From the above, it was determined that the IM test chews yielded significantly reduced gingival and plaque scores, relative to the control and null groups, and significantly reduced calculus scores relative to the null group.

EXAMPLE 2

Animal Study Using Extruded Chews

To further investigate the efficacy of dental compositions according to the present disclosure on the oral health of canines, another thirty day study was conducted on a pool of thirty adult greyhound dogs. This second study was conducted in much the same manner as the study discussed in Example 1, except that the control and test chews were produced via an extrusion process, instead of by an injection molding process.

The compositions of the extruded control chews and extruded test chews are provided in Table 3 below. Like the IM test chews, the extruded test chews were formulated to provide a vitamin C dose of 4 mg/kg body weight, a beta-glucan dose of 2.0 mg/kg body weight, and an HMP dose of 84 mg/kg body weight, assuming an average body weight of 30 kg.

TABLE 3

Composition of the Extruded Control Chews and Extruded Test Chews

| Ingredient | Extruded Control Chew (weight %/lbs) | Extruded Test Chew (weight/lbs) |
| --- | --- | --- |
| Wheat Gluten | 0.880/2.640 | 0.880/2.640 |
| Wheat Starch power | 55.36/166.079 | 51.959/155.877 |
| Rice flour | 0.810/2.430 | 0.810/2.430 |
| White glutinous rice flour | 12.110/36.330 | 12.110/36.330 |
| Cellulose fiber | 0.810/2.430 | 0.810/2.430 |
| Lecithin Powder | 0.810/2.430 | 0.810/2.430 |
| Glycerin | 12.110/36.330 | 12.110/36.330 |
| Guar Gum | 0.810/2.430 | 0.810/2.430 |
| Palatability Enhancer | 12.110/36.330 | 12.110/36.330 |
| Calcium Carbonate | 0.970/2.910 | 0.970/2.910 |
| Chicken Powder | 3.070/9.210 | 3.070/9.210 |
| Tocobiol PV | 0.060/0.180 | 0.060/0.180 |
| Soynatto-F614 | 0.060/0.180 | 0.060/0.180 |
| Nylabone ® vitamin concentrate | 0.070/0.210 | 0.070/0.210 |
| Bacon flavor | 0.240/0.720 | 0.240/0.720 |
| Roast beef flavor | 0.240/0.720 | 0.240/0.720 |
| Chlorophyll liquid | 0.290/0.870 | 0.290/0.870 |
| Water | 3.230/9.690 | 3.230/9.690 |

TABLE 3-continued

Composition of the Extruded Control Chews and Extruded Test Chews

| Ingredient | Extruded Control Chew (weight %/lbs) | Extruded Test Chew (weight/lbs) |
| --- | --- | --- |
| Ascorbic Acid* | 0.00/0.00 | 0.200/0.600 |
| Sodium Hexametaphosphate | 0.00/0.00 | 3.100/9.300 |
| Beta glucans* | 0.00/0.00 | 0.101/0.302 |
| Total | 100.000/300.000 | 100.000/300.000 |

The extruded control chews and extruded test chews were administered to a control group of 10 dogs and a test group of 10 dogs, as described in Example 1. Dental examinations were performed on each animal at the beginning and end of the study. The results are reported in Table 4 below.

TABLE 4

Average Initial and Final Dental Scoring - Extruded Chews

|  | Null Group | | Control Group | | Test Group | |
| --- | --- | --- | --- | --- | --- | --- |
|  | Initial | Final | Initial | Final | Initial | Final |
| Gingival* | | | | | | |
| Mean | 1.20 | 0.77 | 1.22 | 0.73 | 1.02 | 0.62 |
| Standard Deviation | 0.77 | 0.87 | 0.96 | 0.77 | 0.91 | 0.74 |
| Calculus* | | | | | | |
| Mean | 0.00 | 0.94 | 0.00 | 0.69 | 0.00 | 0.39 |
| Standard Deviation | 0.00 | 0.85 | 0.00 | 0.65 | 0.00 | 0.64 |
| Plaque* | 0.00 | | 0.00 | | 0.00 | |
| Mean | 0.00 | 1.92 | 0.00 | 1.67 | 0.00 | 1.51 |
| Standard Deviation | 0.00 | 0.99 | 0.00 | 0.88 | 0.00 | 0.84 |

Figure 6:
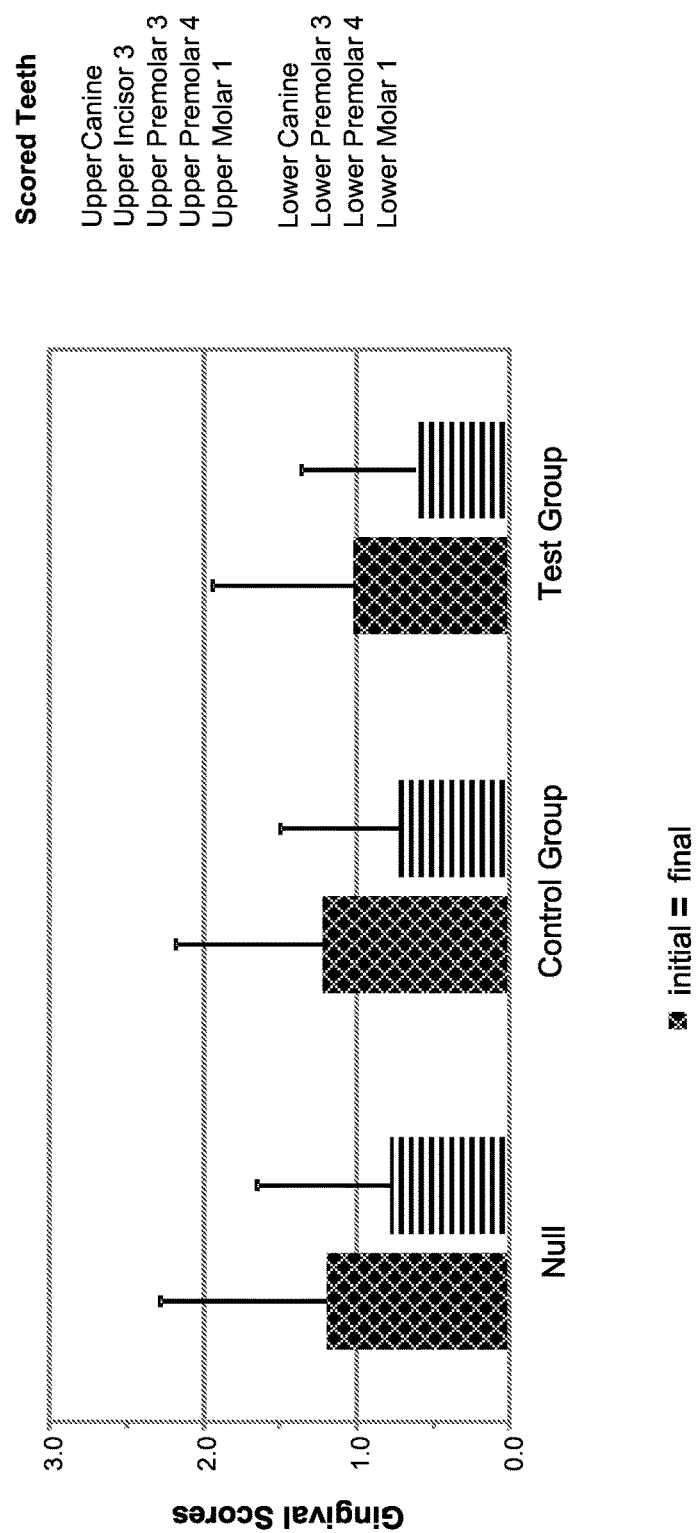
FIG. 6 is a bar graph plotting the gingival scores of dogs that were administered no bone (null), a control bone (control group) group, and a test bone (test group) containing a dental composition in accordance with another embodiment of the present disclosure.
Figure 7:
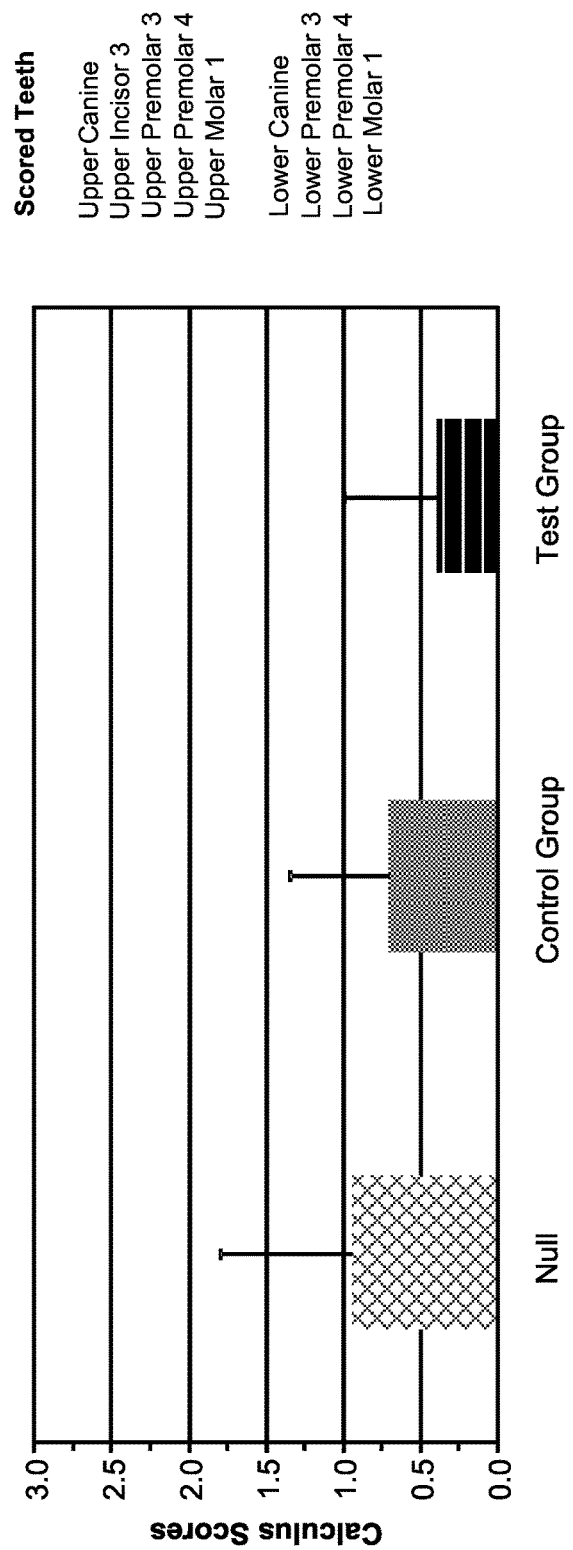
FIG. 7 is a bar graph plotting the final calculus scores of dogs that were administered no bone (null), a control bone (control group), and a test bone (test group) containing a dental composition in accordance with another embodiment of the present disclosure.
Figure 8:
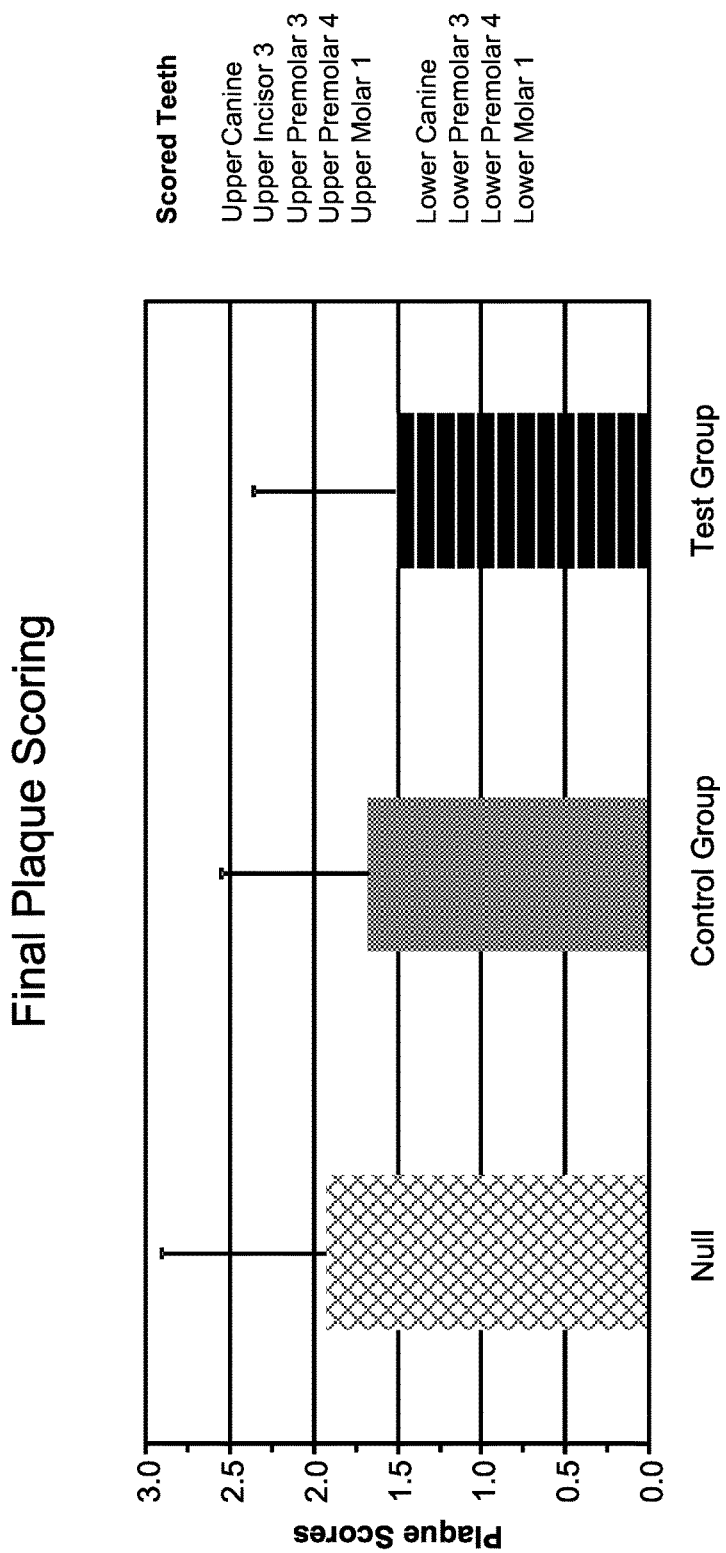
FIG. 8 is a bar graph plotting the final plaque scores of dogs that were administered no bone (null), a control bone (control group), and a test bone (test group) containing a dental composition in accordance with another embodiment of the present disclosure.

*By convention, gingival, calculus, and plaque scores range from 0 to 3
These results are presented graphically in FIGS. 6-8.

Figure 9:
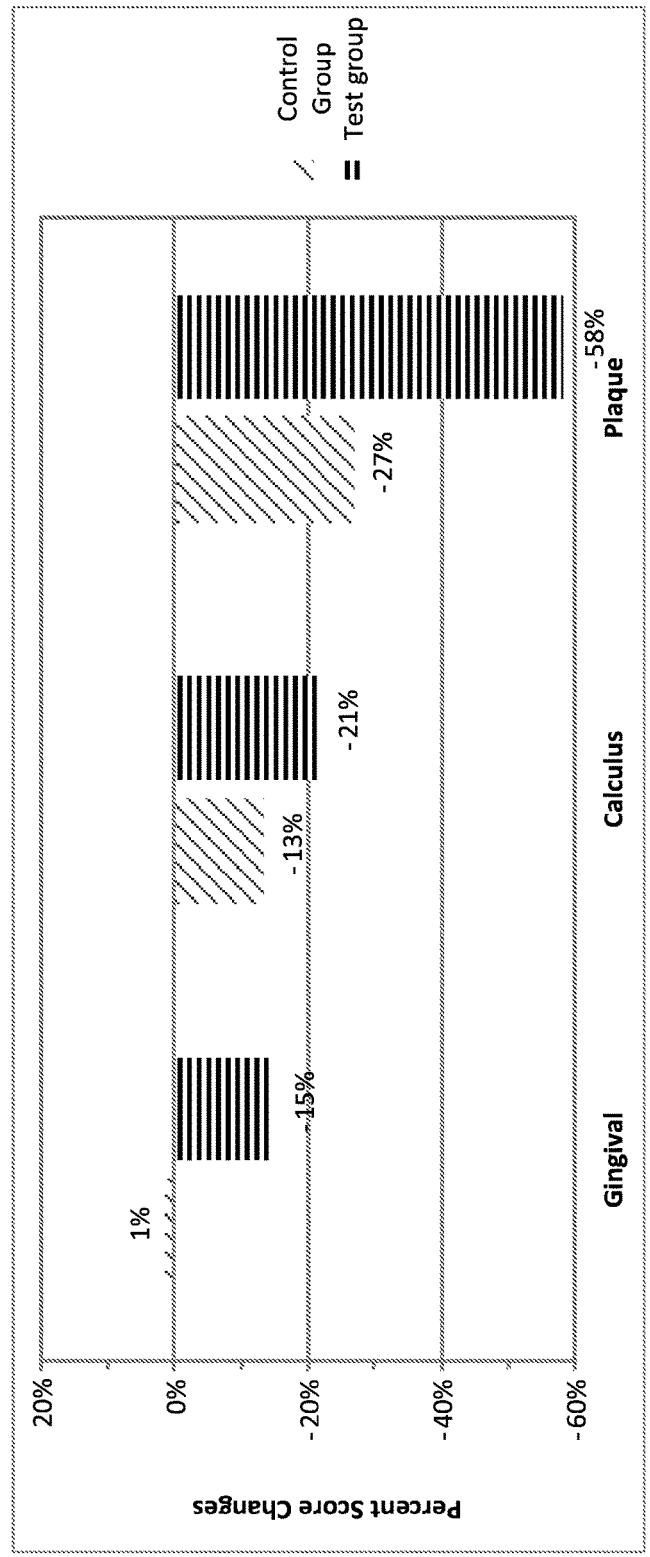
FIG. 9 is a bar graph plotting the gingival, plaque, and calculus score reductions of dogs that were administered a control bone (control group), and a test bone (test group) containing a dental composition in accordance with another embodiment of the present disclosure, relative to the corresponding scores of dogs that were administered no bone (null).
Figure 10:
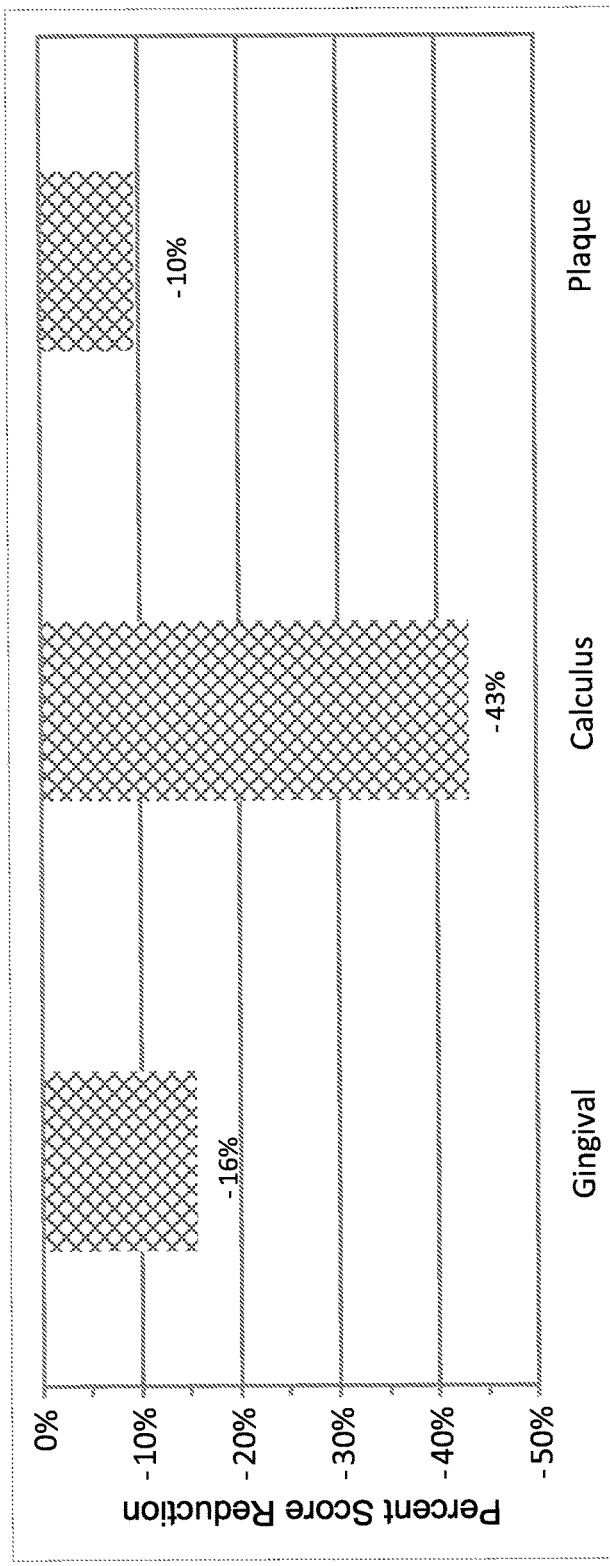
FIG. 10 is a bar graph plotting the difference between the gingival, plaque, and calculus scores of dogs administered a test bone (test group) containing a dental composition in accordance with another embodiment of the present disclosure, and corresponding scores of dogs that were administered a control bone (control group).

As in example 1, the performance of the extruded control chews was determined by comparing the average final dental scoring (gingivitis, calculus, and plaque) of the control group to the average final dental scores of the null group. Likewise, the performance of the extruded test chews was determined by comparing the average final dental scores of the test group to the average final dental scores of the null group. The results are plotted in FIGS. 9 and 10.

As shown, relative to the null group, dogs in the test group exhibited a 15% decrease in gingival score, whereas dogs in the control group exhibited a 1% increase in gingival score. In the case of plaque, dogs in the test group exhibited a 21% reduction in plaque score relative to the null group, whereas dogs in the control group exhibited a 13% reduction in plaque score. Finally, dogs in the test group exhibited a 58% reduction in calculus score relative to the null group, whereas dogs in the control group exhibited a 27% reduction in calculus score. This data indicates that the extruded test chews prevented or removed 16% more gingivitis, 8% more plaque, and 31% more calculus than the extruded control chews.

From the above, it was determined that the extruded test chews yielded significantly reduced gingival, plaque and calculus scores, relative to the control and null groups.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for treating at least one of gingivitis and dental calculus in an animal, comprising:
   administering a dental composition to a mouth of said animal, the dental composition comprising:
   ascorbic acid in an amount ranging from greater than 0 to about 5 weight %;
   at least one hexametaphosphate (HMP) in an amount ranging from greater than 0 to about 5 weight %; and
   at least one beta glucans extracted from a yeast in an amount ranging from about 0.1 weight % to about 0.5 weight %;
   a base composition comprising at least one primary ingredient in an amount greater than or equal to about 30 weight % of said dental composition, wherein said primary ingredient is selected from the group consisting of starches, rubbers, composites, polymers, wood, and combinations thereof.

2. The method of claim 1, wherein said beta glucans consists of beta glucans extracted from saccharomyces cerevisae.

3. The method of claim 1, wherein said dental composition further comprises a mushroom matrix.

4. The method of claim 1, wherein said primary ingredient comprises at least one starch.

5. The method of claim 1, wherein said dental composition comprises said HMP in an amount ranging from about 1 to about 4 weight %.

6. The method of claim 1, wherein said dental composition comprises:
   said ascorbic acid in an amount ranging from about 0.1 to about 0.5 weight %;
   said HMP in an amount ranging from about 2 to about 4 weight %; and
   said at least one beta glucans in an amount ranging from about 0.1 weight % to about 0.25 weight %.

7. The method of claim 1, wherein said dental composition is incorporated into at least one of a dentifrice, a toothpaste, a chew, and an edible product.

8. The method of claim 1, wherein said dental composition when administered to said mouth of said animal delivers:
   said ascorbic acid at a dosage rate ranging from about 2 to about 6 milligrams per kilogram of body weight of said animal;
   said at least one HMP at a dosage rate of about 50 to about 100 milligrams per kilogram of body weight of said animal; and
   said at least one beta glucans at a dosage rate of greater than 0 to about 3 milligrams per kilogram of body weight of said animal.

* * * * *